(12) United States Patent
Sifers et al.

(10) Patent No.: US 9,955,829 B2
(45) Date of Patent: May 1, 2018

(54) METHOD AND APPARATUS FOR CONTROLLING ODORS

(71) Applicant: ENVIRONMENTAL PURIFICATION, LLC, Leawood, KS (US)

(72) Inventors: Don S. Sifers, Fairway, KS (US); Kent A. Pennybaker, Lawrence, KS (US)

(73) Assignee: Environmental Purification, LLC, Leawood, KS (US)

( * ) Notice: Subject to any disclaimer, the term of this patent is extended or adjusted under 35 U.S.C. 154(b) by 257 days.

(21) Appl. No.: 14/995,663

(22) Filed: Jan. 14, 2016

(65) Prior Publication Data

US 2016/0262584 A1 Sep. 15, 2016

Related U.S. Application Data

(63) Continuation of application No. 14/665,712, filed on Mar. 23, 2015, now Pat. No. 9,265,389, which is a
(Continued)

(51) Int. Cl.
*A47K 17/00* (2006.01)
*F23G 7/07* (2006.01)
(Continued)

(52) U.S. Cl.
CPC ............... *A47K 17/00* (2013.01); *A61L 9/00* (2013.01); *A61L 9/032* (2013.01); *A61L 11/00* (2013.01);
(Continued)

(58) Field of Classification Search
CPC . A47K 17/00; A61L 9/00; A61L 11/00; F23G 7/07
See application file for complete search history.

(56) References Cited

U.S. PATENT DOCUMENTS

| 539,459 A | 5/1895 | Webb |
| 1,775,565 A | 9/1930 | Kessler |

(Continued)

FOREIGN PATENT DOCUMENTS

| EP | 0331192 | 4/1992 |
| EP | 0595098 | 5/1994 |

(Continued)

OTHER PUBLICATIONS

International Search Report and Written Opinion for International Application No. PCT/US07/19038 dated Jan. 31, 2008.
(Continued)

*Primary Examiner* — Sean E Conley
(74) *Attorney, Agent, or Firm* — Alson & Bird LLP

(57) ABSTRACT

Methods and apparatus for controlling odors in an enclosed space, such as a pit latrine, include providing an oxidizer, such as a catalytic heater and an optional mechanical ventilation unit, such as an inline fan, both flow connected to a vault (pit) of the latrine. The heater is also connected to a source of fuel, for example, propane. Fresh air is drawn through vents in the latrine housing and thereafter through toilets in the latrine and through the vault, providing oxygen for the reaction. The fan and/or oxidation process draws both fresh air and accompanying odorous compounds directly from the latrine and into the oxidizer wherein the odorous components are substantially destroyed.

17 Claims, 5 Drawing Sheets

Related U.S. Application Data continuation of application No. 14/300,818, filed on Jun. 10, 2014, now Pat. No. 9,017,606, which is a continuation of application No. 11/897,452, filed on Aug. 30, 2007, now Pat. No. 8,784,739.

(60) Provisional application No. 60/842,828, filed on Sep. 7, 2006.

(51) Int. Cl.
  *A61L 11/00* (2006.01)
  *E03D 9/04* (2006.01)
  *A61L 9/00* (2006.01)
  *A61L 9/03* (2006.01)

(52) U.S. Cl.
  CPC .............. *E03D 9/04* (2013.01); *F23G 7/07* (2013.01); *Y10T 29/49826* (2015.01)

(56) References Cited

U.S. PATENT DOCUMENTS

| | | | |
|---|---|---|---|
| 3,337,455 A | 8/1967 | Wilson et al. | |
| 3,597,769 A | 8/1971 | Brainard, II et al. | |
| 3,655,053 A | 4/1972 | Hugin | |
| 3,893,810 A | 7/1975 | Lientz | |
| 3,904,351 A | 9/1975 | Smith et al. | |
| 3,914,088 A | 10/1975 | Hyuck | |
| 3,921,227 A | 11/1975 | Blantenship | |
| 3,974,075 A | 8/1976 | Saigh et al. | |
| 4,038,032 A | 7/1977 | Brewer et al. | |
| 4,053,399 A | 10/1977 | Donelly et al. | |
| 4,200,940 A | 5/1980 | Buchanan | |
| 4,559,006 A | 12/1985 | McGill et al. | |
| 4,600,557 A | 7/1986 | Spitz | |
| 4,634,369 A | 1/1987 | McGill et al. | |
| 4,900,244 A | 2/1990 | Keller et al. | |
| 4,909,948 A | 3/1990 | Eichelberger, Sr. | |
| 4,957,710 A | 9/1990 | Nagai et al. | |
| 5,037,293 A | 8/1991 | Kirby | |
| 5,131,888 A | 7/1992 | Adkins, II | |
| 5,184,355 A | 2/1993 | Taguchi et al. | |
| 5,221,523 A | 6/1993 | Miles et al. | |
| 5,257,466 A | 11/1993 | Kishi | |
| 5,265,544 A | 11/1993 | Bigelow et al. | |
| 5,295,448 A | 3/1994 | Vickery | |
| 5,357,880 A | 10/1994 | Kishi | |
| 5,460,789 A | 10/1995 | Wilhelm | |
| 5,462,676 A | 10/1995 | Pitts | |
| 5,484,574 A | 1/1996 | MacAluso et al. | |
| 5,519,897 A | 5/1996 | DeSimone | |
| 5,562,442 A | 10/1996 | Wilhelm | |
| 5,564,133 A | 10/1996 | Kishi | |
| 5,575,082 A | 11/1996 | Kishi | |
| 5,983,834 A | 11/1999 | Tai | |
| 6,045,355 A | 4/2000 | Chapman et al. | |
| 6,190,566 B1 | 2/2001 | Kolber | |
| 6,207,106 B1 | 3/2001 | Kurokawa et al. | |
| 6,231,334 B1 | 5/2001 | Bussman et al. | |
| 6,276,304 B1 | 8/2001 | Tai | |
| 6,278,304 B1 | 8/2001 | Tai | |
| 6,321,687 B1 | 11/2001 | Lemmon et al. | |
| 6,569,673 B1 | 5/2003 | Nakagawa et al. | |
| 6,698,383 B1 | 3/2004 | Terwort et al. | |
| 6,840,761 B2 | 1/2005 | Hong et al. | |
| 6,932,593 B2 | 8/2005 | Chapman | |
| 2004/0040516 A1 | 3/2004 | Jensen | |
| 2005/0273917 A1 | 12/2005 | Lapossy | |
| 2006/0064910 A1 | 3/2006 | Shankle | |
| 2009/0301402 A1 | 12/2009 | Devine et al. | |

FOREIGN PATENT DOCUMENTS

| | | |
|---|---|---|
| JP | 05222754 | 8/1993 |
| JP | 08238034 | 9/1996 |
| JP | 08326119 | 12/1996 |
| JP | 2003293428 | 10/2003 |
| KR | 2005046505 | 5/2005 |
| WO | WO 03089375 | 10/2003 |

OTHER PUBLICATIONS

In-Depth Design and Maintenance Manual for Vault Toilets Brochure, Briar Cook, Civil Engineer, Program Leader, Recreation, Technology & Development Center San Dimas, California, pub. 1991.

Installation, Operation & Maintenance of Catalytic Heaters Brochure, Catalytic Industrial Group, Inc., pub. May 2004.

How Good? Twice as Good. Brochure, Bruest Catalytic Heaters, no publication date.

METHOD AND APPARATUS FOR CONTROLLING ODORS

CROSS-REFERENCE TO RELATED APPLICATIONS

This application is a continuation of U.S. patent application Ser. No. 14/665,712, filed Mar. 23, 2015, now U.S. Pat. No. 9,265,389, issued Feb. 23, 2016, which application is a continuation of U.S. patent application Ser. No. 14/300,818, filed Jun. 10, 2014, now U.S. Pat. No. 9,017,606, issued Apr. 28, 2015, which application is a continuation of U.S. patent application Ser. No. 11/897,452, filed Aug. 30, 2007, now U.S. Pat. No. 8,784,739, issued Jul. 22, 2014, which claims priority to U.S. Provisional Application No. 60/842,828, filed Sep. 7, 2006, each of which is incorporated by reference herein in its entirety.

BACKGROUND OF THE INVENTION

The present invention is directed to improved apparatus and methods for controlling fecal and other human or animal body odors from a substantially enclosed space and in particular for withdrawing and incinerating odorous gasses from pit latrines.

Pit latrines suffer from bad odor due to the confined nature of the pit and the waste deposited into the pit. The addition of heat during the busy summer months amplifies the odor problem. Often, pit latrines are located in remote areas. Thus, it may not be possible to equip a pit latrine with sufficient ventilation, for example, elevated stacks, to reduce latrine odor. Even in situations where electricity is available, mechanical ventilation, such as an exhaust fan, may remove some of the latrine odor from an enclosed area, but then merely move the odor to another area that can still create an undesirable odor in a public place, such as a park located near the pit latrine. Therefore, it would be desirable to have a method and relatively simple apparatus for deodorizing a pit latrine that does not merely move the offending odors from one location to another.

It is known in the art to remove noxious gas, such as sewer gas, by flaring the gas. A variety of patent publications disclose burners for igniting noxious gasses from, for example, sewers, mines and landfills. However, the use of open flames are not desirable in remote settings and/or settings visited by the general population, such as public parks.

SUMMARY OF THE INVENTION

Methods and apparatus according to the invention for controlling fumes from an enclosed space, such as a pit latrine, having a waste reservoir or vault connected to one or more toilets includes directly connecting the vault to an incinerator or oxidizer. Preferably, the incinerator is flameless. Most preferably the incinerator is a catalytic heater that utilizes an easily obtained fuel, such as propane, for the oxidation process. As an oxygen source for the process, fresh air (from existing vents in the latrine housing) and noxious latrine fumes are drawn into the incinerator through the toilets and then the latrine vault by the oxidation process being performed in the incinerator. A ventilation unit such as an in-line fan can be utilized with the process to increase the speed and/or volume of air flow and accompanying odors drawn from the vault into the incinerator. The latrine is thus ventilated with only fresh air, with positive air flow being pulled through the toilets. Furthermore, hot deodorized gas that leaves the incinerator may be used directly or indirectly to warm the pit latrine housing in cold weather.

OBJECTS AND ADVANTAGES OF THE INVENTION

Therefore, objects of the present invention include: providing methods and apparatus for deodorizing the user space of pit latrines and other enclosed spaces located adjacent to fecal matter; providing such methods and apparatus that safely remove noxious odors from a public user space through the pit latrine vault; providing such methods and apparatus that oxidize pit latrine gas without using a flame; providing such methods and apparatus that utilize commercially available flame-less heaters; providing such methods and apparatus that further utilize mechanical ventilation; providing such methods and apparatus that are inexpensive to produce and especially well adapted for the intended usage thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

DETAILED DESCRIPTION OF THE INVENTION

Figure 1:
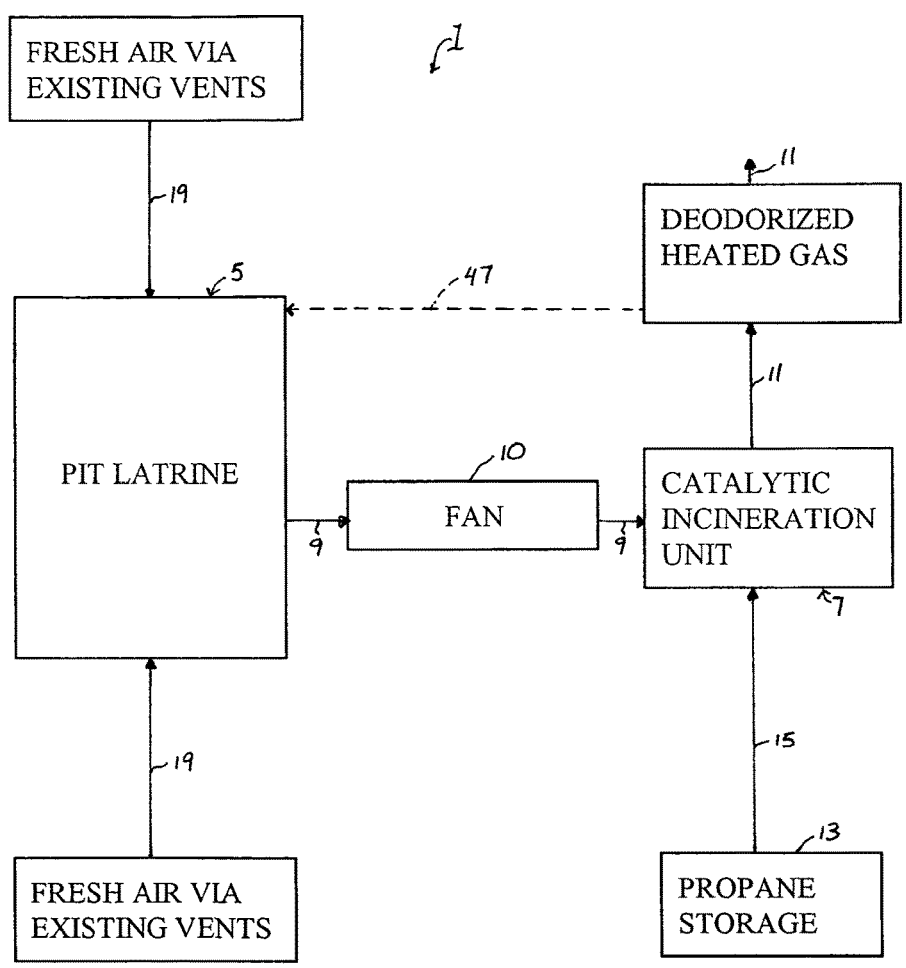
FIG. 1 is a general schematic representation of a process according to the invention.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

A system generally indicated by the reference numeral 1 for controlling odors in a public user space of a pit latrine is illustrated in FIGS. 1-5. The system includes a pit latrine, generally 5, an incineration or oxidation unit, generally 7, a latrine gas supply conduit 9 equipped with a mechanical ventilation unit such as an in-line fan 10 powered by a motor 10A, the conduit 9 connecting the latrine 5 with the incineration unit 7, and a conduit or stack 11 for removal of substantially oxidized and deodorized gas from the incineration unit 7. A fuel storage unit 13 is connected to the incineration unit 7 by a conduit 15. Typically, the pit latrine 5 is already in existence and fresh air for the oxidation process enters through a housing 17 that defines an enclosed user space 18 of the latrine 5. Specifically, the air enters into the space 18 through one or more existing vents 19 located on the housing 17. In the illustrated embodiment, a control system 20 communicates with the unit 7 and the fan motor 10A and is powered by a battery system 21 that is recharged by a solar panel 22. The control system 20 may be utilized to cycle the fan 10 and incineration unit 7 on a time dependent schedule to optimize fuel usage.

As indicated above, the system 1 according to the invention may be used with an existing pit latrine or incorporated into a new pit latrine system. It is foreseen that a system and process according to the invention may also be utilized with a portable toilet. Additionally, it is foreseen that such a system and process according to the invention may be used to deodorize enclosed spaces for holding animals, such as pig operations.

Figure 2:
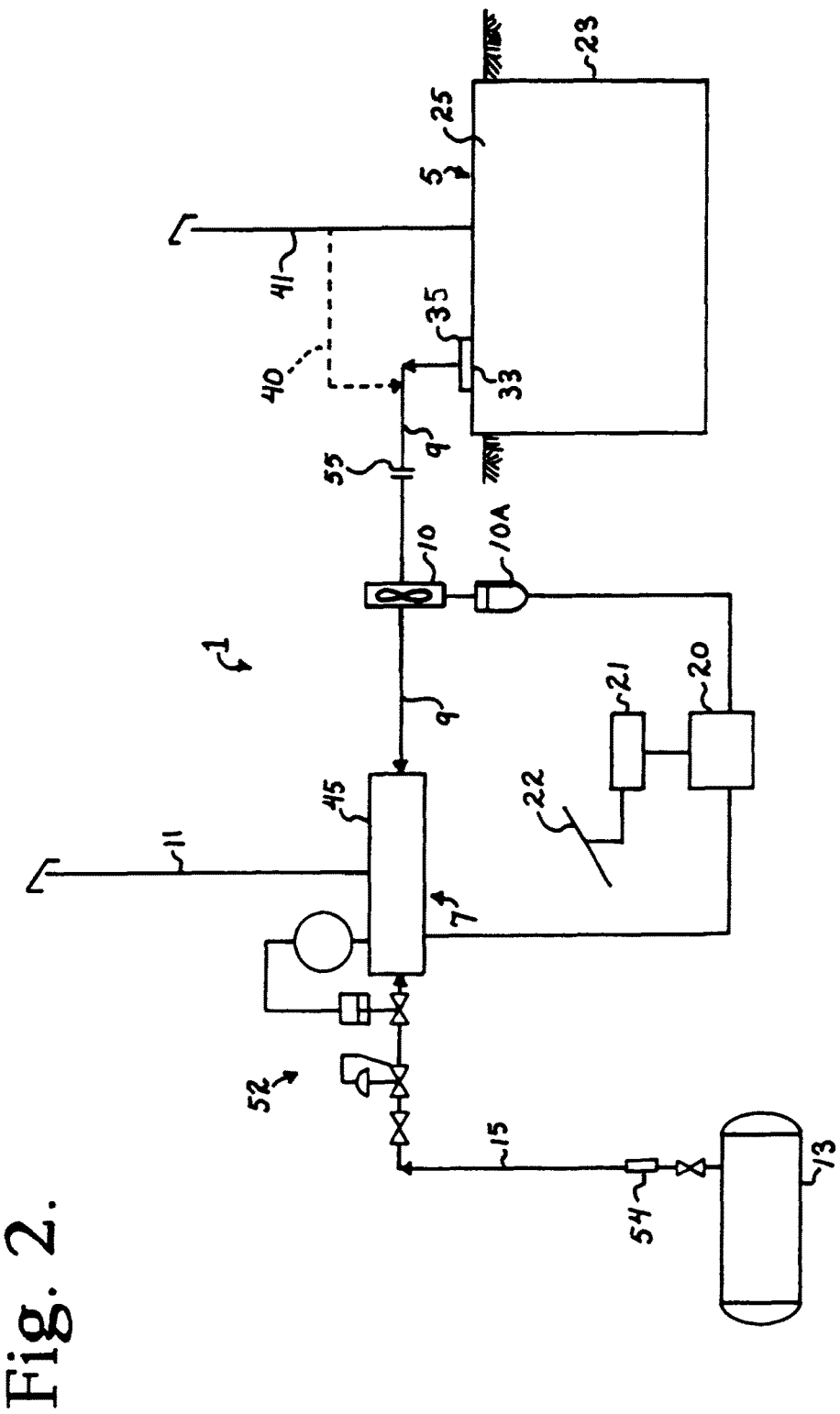
FIG. 2 is a more detailed schematic view of a process and apparatus according to the invention.
Figure 4:
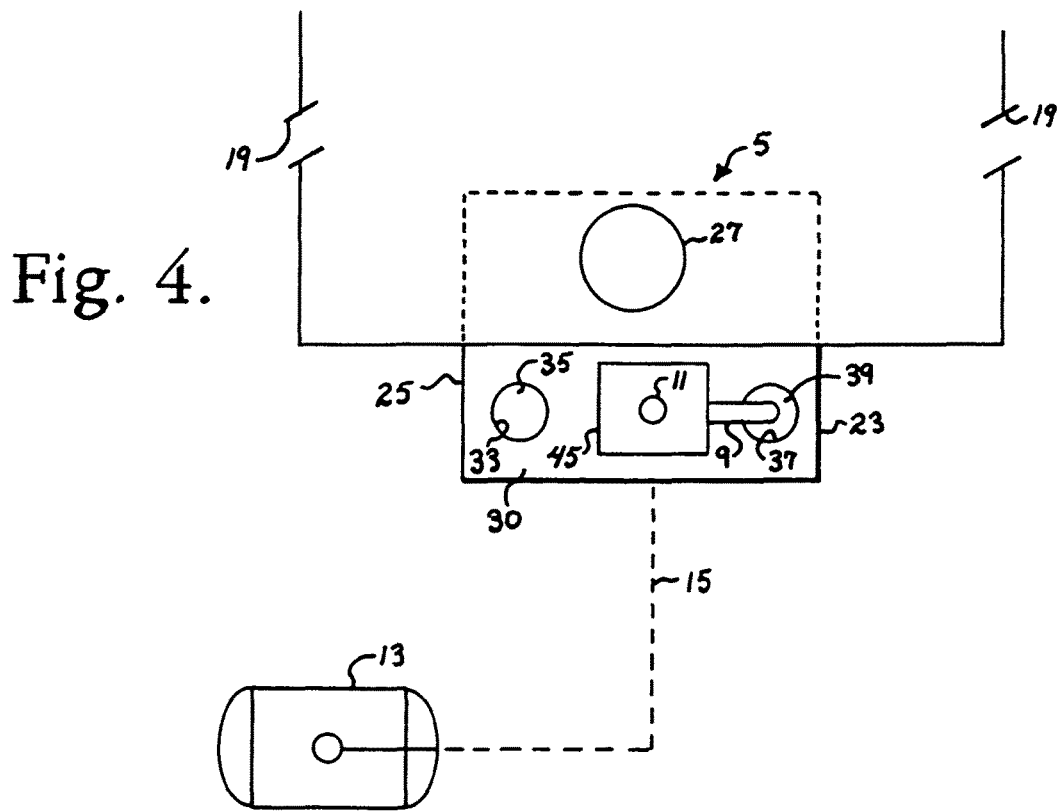
FIG. 4 is a partially schematic top plan view of the apparatus and method of FIG. 3.

A pit latrine 5 typically includes a pre-manufactured concrete structure 23 forming a vault or waste reservoir chamber 25, the structure being installed into the ground. The housing 17 that provides the enclosed public use space 18 is then built over the vaulted structure 23. One or more toilets 27 located in the space 18 empty directly into the vault 25. A portion 30 of the structure 23 is typically outside the housing 17 and includes a "pump-out" opening 33 communicating with the vault 25 that is typically covered by a man-hole cover 35. The pump-out opening 33 is modified (as shown in FIG. 2) or a second opening 37 (as shown in FIG. 4) is formed for direct gas-flow communication with the vault 25. The opening 37 includes a cover 39 attached to the latrine gas conduit 9 resulting in the conduit 9 being directly flow connected to the vault 25 and the oxidation unit 7. With reference to FIG. 2, alternatively, the latrine gas conduit 9 may be connected via a conduit 40 (shown in dotted lines) to a new or existing vault vent stack 41.

Gas from a pit latrine typically has a composition identified in Table I below. Thus, such gas is rich in oxygen, with the odorous compounds or components being present in relatively small amounts. According to an aspect of the invention, the noxious compounds present in the air located in the latrine are oxidized using a catalytic incinerator with air being supplied for the oxidation process. It is noted that it has been found that complete oxidation of the noxious compounds is not required for adequate odor removal. For example, in an embodiment according to the invention wherein the fan 10 is included, the fan aids in removing air from the public user space. Then, the noxious compounds found in the air are either fully or partially oxidized in the catalytic incinerator. Any remaining noxious compounds rise high above the unit 7 due to the higher temperature of the flue gas as compared to the surrounding air, and are dispersed without causing odor problems in nearby areas. Catalytic incinerators operate very similar to thermal incinerators, with the primary difference that the gas to be oxidized passes through a catalyst bed rather than the flames of a thermal heater. The catalyst has the effect of increasing the oxidation reaction rate, enabling conversion at lower reaction temperatures than in thermal incinerator units. Thus, the oxidation is performed at a safer temperature and the catalytic combustion of the fuel typically is more efficient than when burned using a flame.

TABLE I

| PIT GAS - COMPOSITION (MOLE %) | |
| --- | --- |
| $N_2$ | 80.6595 |
| $O_2$ | 19.0 |
| $C_1$ (HC's) | (ND-3000 ppm) 0.30 |
| $CO_2$ | (400 ppm) 0.04 |
| $NH_3$ | (4 ppm) 0.0004 |
| $H_2S$ | (ND-0.5 ppm) 0.00005 |
| RSH | (ND-0.1 ppm) 0.00001 |
| $SO_2$ | (ND-0.1 ppm) 0.00001 |
| Benzene | (ND-0.5 ppm) 0.00005 |
| Total | 100.00 |

With particular reference to FIGS. 2-5, according to the invention, a preferred incineration/oxidation unit 7 according to the invention for deodorizing a public use space of a pit latrine is a catalytic heater 45, available, for example, from Bruest Catalytic Heaters, Independence, Kans. The catalytic heater 45 is a conventional gas catalytic heater known in the art that includes a fuel supply inlet and a catalyst bed that utilizes a platinum or other transition metal catalyst to generate heat from a flame-less catalytic reaction, between, for example propane and oxygen. Such heaters are typically used for space heating and industrial instrument heating. The catalytic heater 45 is commercially designed to utilize a readily available fuel gas, such as propane, ethanol or natural gas, to produce heat and thus to provide an efficient alternative heating source wherever flame-less heat is desired. Without a flame, the fuel gas is oxidized (catalytic combustion), in the presence of oxygen, to form carbon dioxide, water vapor and heat. According to the invention, the catalytic heater 45 is utilized to heat and oxidize noxious gas from a latrine wherein the oxygen source for the reaction performed in the catalytic heater 45 is air drawn through the vents 19 of the housing 17, into and through the toilet 27 or toilets, through the latrine vault 25, and out of the vault opening (33 or 37 or stack 41). Such oxygen source also advantageously includes the odorous components or compounds listed in Table I above that are present within the public use space 18, the toilets 27 and the vault 25. In the illustrated embodiment, the fuel is propane drawn from the fuel tank 13 through the conduit 15 into the catalytic heater 45. During the oxidation process of the propane, odorous components in the air stream from the latrine vault are converted into less odorous or non-odorous compounds via oxidation.

Sufficient heat evolves from such process to raise the temperature of the catalytic bed of the heater, and thus oxidation continues as long as a fuel gas (such as propane) and oxygen from the latrine gas (air+odorous components) are supplied. Therefore, it is possible to initialize the oxidation process by heating the catalyst bed using, for example, an electric resistance heating element. Thereafter, the resistance heater is not needed. It is also foreseen that the hot gas exiting the catalytic heater may be used to preheat gas entering the heater, if desired. Furthermore, with reference to FIG. 1, alternatively, a hot gas stream 47 exiting the catalytic heater may be used directly or indirectly (e.g. heat exchanger) to heat the public use space 18 of the pit latrine 5 during cold winter months.

In the illustrated embodiment, the fan 10 is disposed in the line 9 located between the vault 25 of the pit latrine 5 and the catalytic heater 45 and draws air out of the vault 5 and into the heater 45. Thus, the fan provides advantageous positive air flow through the enclosed public user space 18 and through the toilet 27 or toilets, directing fecal odor away from people using the toilet 27. The fan 10 further aids in propelling a deodorized air stream through the heater 45 and out the stack 11. The fan 10 can be operated with or without the heater 45 being in operation, providing some relief from fecal odors in the enclosed public use space 18 even when the heater 45 is not in operation. The illustrated fan 10 is powered by batteries 21 that are charged by solar power 22 or alternatively, an electrical connection. When the heater 45 is operating, the heated off gasses flowing out of the catalytic heater 45 will rise to a sufficient elevation to allow for dispersion of any un-reacted noxious compounds at a distance from the latrine and surrounding public use area.

In other embodiments according to the invention, one large catalytic heater 45 or two or more smaller catalytic heaters 45 are utilized without using the fan 10 to draw the air and odorous components from the latrine vault 25. In such embodiments, as long as propane is fed into the catalytic heater 45, the oxidation of the propane in the heater 45 draws air (oxygen) from the vault 25 through the line 9 and into the heater 45. Thus, air is advantageously positively drawn into and through the toilets 27, drawing fresh air into the enclosed public use space 18 defined by the housing 17 and keeping fecal and other odors away from the users of the toilets 27 located within the enclosed space 18. Furthermore, the out-gas conduit or vent stack 11 may be designed to aid in drawing a natural draft to draw the latrine gas out of the pit latrine. It is believed that the stack 11 may also create a slight vacuum in the vault 25 that causes air from outside the vault to be drawn into the latrine building through the vents 19 and into the vault 25 through the toilet or toilets 27.

In the illustrated embodiment, fuel for the heater 45 is preferably propane stored in the receptacle 13 that is typically a household or industrial sized storage tank with the size being determined by how often the storage tank is to be re-supplied. Other fuels, such as natural gas, ethanol, butane, hydrogen and methanol may also be used in processes of the invention.

As illustrated in FIG. 2, apparatus according to the invention preferably include certain safety features, such as a check valve 50 to prevent back flow of fuel (e.g. propane) into the vault 25 and isolation valves and regulators, generally 52, typically supplied by the catalytic heater vendor. Other details of the illustrated system include an excess flow valve 54 downstream of the fuel storage tank 13 and a coupling 55 near the vault structure 23, allowing for the removal of the man-hole cover 35.

Figure 3:
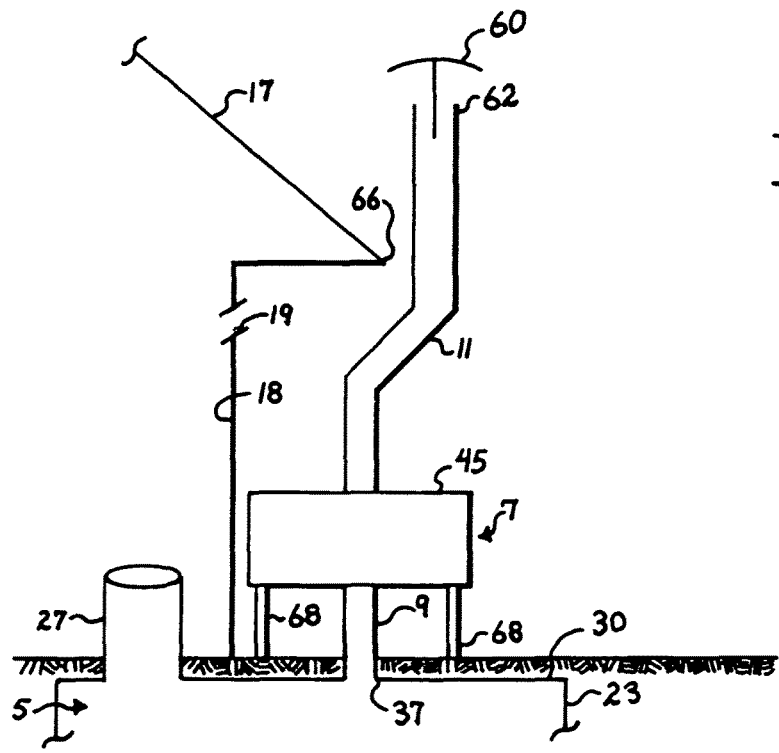
FIG. 3 is a partially schematic side elevational view of an apparatus and method of the invention that includes a vault pump-out connection and grade mounted unit.
Figure 5:
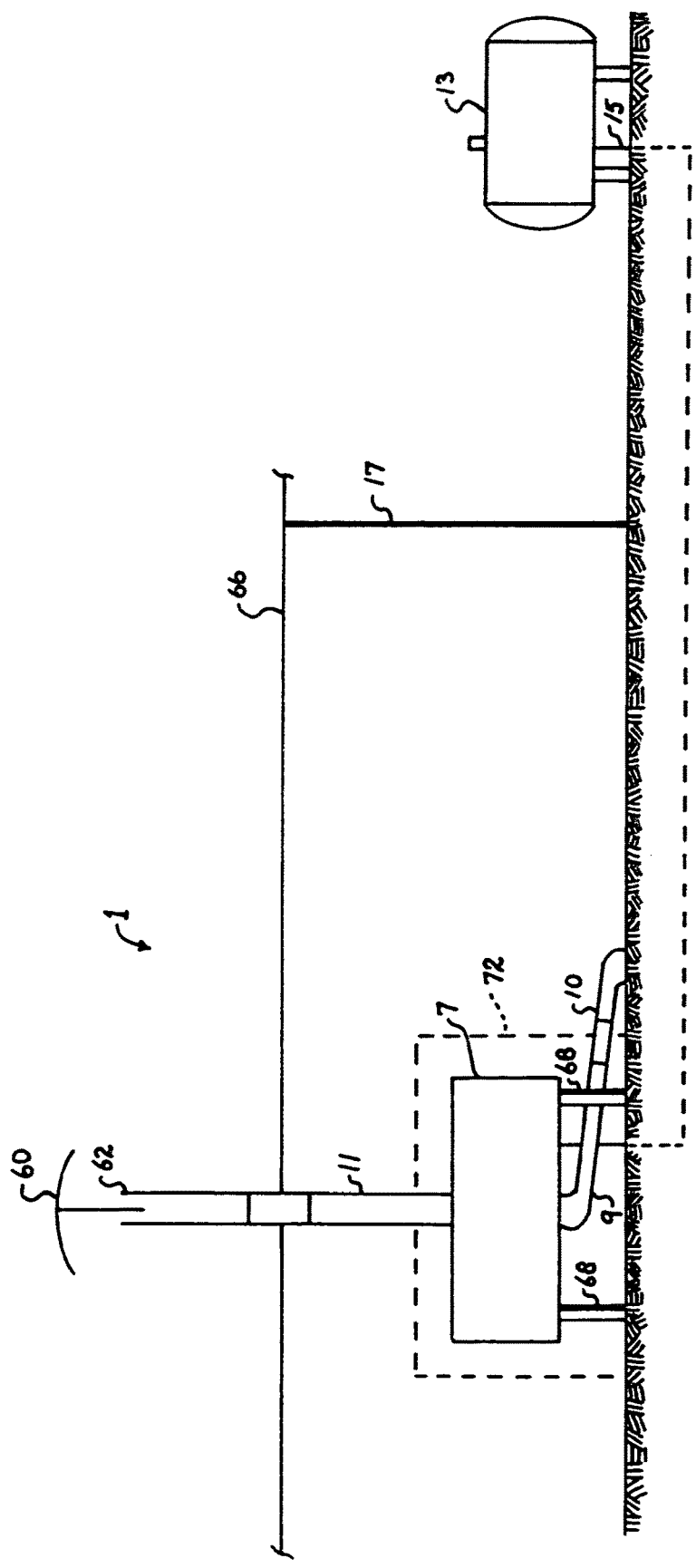
FIG. 5 is a partially schematic front elevational view of the apparatus and method of FIG. 3.

With reference to FIGS. 3-5, other features of the illustrated apparatus according to the invention include a rain cap 60 disposed near a top 62 of the vent stack 11. The vent stack 11 is insulated and extends above the roof eave 66. The fuel supply line 15 is preferably buried. The heater 45 is preferably mounted on a stand 68 so as to be spaced from the top of the concrete pit latrine structure 30. The illustrated heater 45 may be protected by a two-part (clam-shell) cabinet 72 that may be locked. In other embodiments according to the invention, the heater 45 is mounted on the roof of the housing 17 or the stand 68 is elongate, so that the heater 45 is mounted at an elevation at or above the roof line 66. Such mounting improves the security of the system by reducing the likelihood of tampering.

Table II sets forth additional details of the heater 45, fuel storage 13 and conditions of operation for the illustrated embodiment according to the invention:

TABLE II

SAMPLE APPARATUS/OPERATING CONDITIONS

| Incinerator | |
|---|---|
| Type: | Catalytic |
| Pre-Heat: | Internal (325-350° F.) Only for start-up |
| Heat Flux: | 6000 Btu/ft$^2$ design/3000 Btu/ft$^2$ turndown |
| Turndown: | 2:1 |
| Duty: | TBD - Dependent on latrine size/application |
| NORM Temp: | about 400° F. (with fan) |
| Max Temp: | about 850° F. |
| Excess O$_2$ | TBD by calculations |
| Fuel | |
| Type: | HD-5 Propane (94% C3, 5% C2, 1% i-C4) |
| Storage: | 250 gals/500 gals depending upon difficulty of re-filling Provided by local propane supplier |
| Controls: | Regulator and other necessary controls provided by supplier |
| Pressure: (supply) | 100-250 psig - dependent upon ambient temperature |
| Pressure: (heater) | 11 in H2O as regulated at the heater |
| Local Conditions | |
| Temperature: | −20 to 110° F. |
| Elevation: | 0 to 4500 ft above MSL Heater de-rated 4% per 1000 ft above 4500' |
| Humidity: | 0 to 100% |
| Fan | |
| Volume: | TBD for each application |
| Power: | DC |
| Controls | |
| PLC controls for scheduling of heater/fan cycles | |
| Power: | 110 VAC or solar panel |

Figure 6:
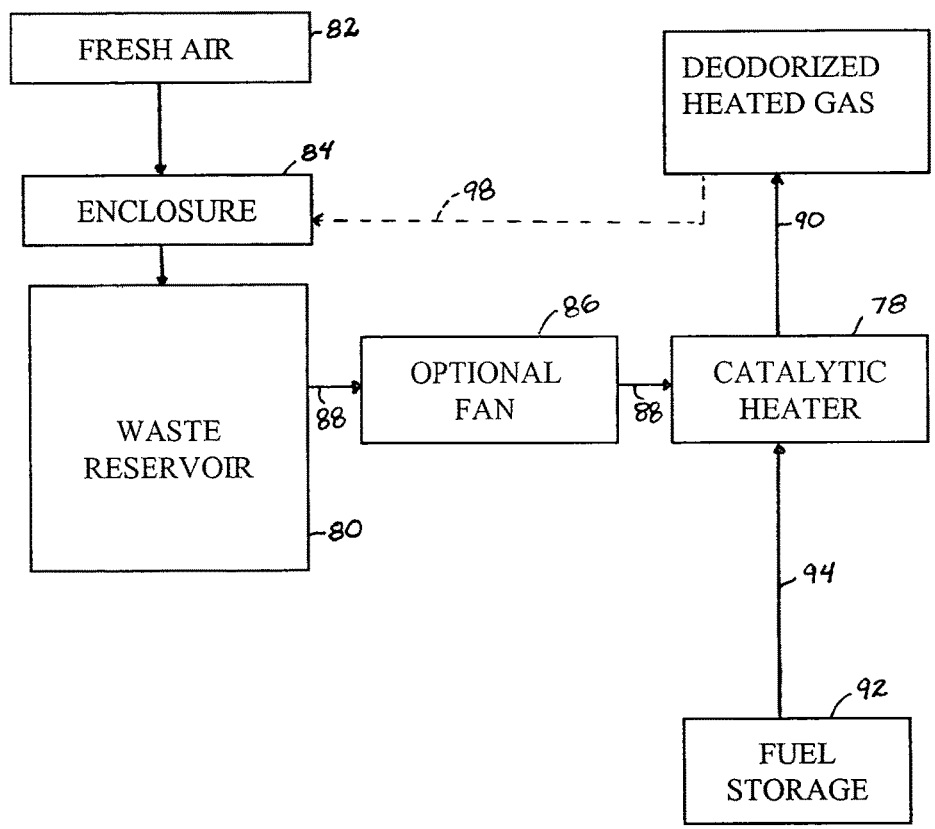
FIG. 6 is another general schematic representation of a process according to the invention.

With reference to FIG. 6, as previously mentioned, process and apparatus according to the invention may be utilized to remove fecal and other human body or animal odors from a substantially enclosed space other than pit latrines. For example, a catalytic heater 78 or series of heaters identical or similar to the heater 45 previously described herein may be directly flow connected to a variety of waste reservoirs or containment members. For example, a small catalytic heater may be directly flow connected to a waste pail or lower waste container of a portable toilet. Or, on the large end, one or more heaters 78 may be flow connected to a waste reservoir 80 or pit located beneath or adjacent to a substantially enclosed space 84 of a pig or other confined animal feeding operation. The process illustrated in FIG. 6 is otherwise the same as described above with respect to the pit toilet system 1. Fresh air 82 is drawn into and through the enclosed area 84 and across or through the pit or waste reservoir 80 and into the heater 78. A ventilation system, such as an in-line fan 86 similar to the fan 10 previously described herein may be located in a conduit 88 flow connecting the gasses from the waste reservoir 80 to the catalytic heater 78. The system includes a conduit or stack 90 for removal of substantially oxidized and deodorized gas from the unit 78. A fuel storage unit 92 for propane or other types of fuel previously described herein is connected to the unit 78 by a conduit 94. As with the system 1, heated off-gasses flowing through a line 98 may be directed toward or otherwise used to heat the enclosure 84.

It is to be understood that while certain forms of the present invention have been illustrated and described herein, it is not to be limited to the specific forms or arrangement of parts described and shown.

What is claimed is:

1. A method of controlling gases in a vault, wherein the method comprises:
   providing a system for drawing air from the vault, the system comprising:
   a flameless heater;
   a first conduit positioned between the vault and the flameless heater, such that the flameless heater is in fluid communication with the vault via the first conduit; and
   a second conduit connected to the flameless heater, wherein the second conduit is configured to emit heated air from the flameless heater to an external environment;
   heating air with the flameless heater to lower an air pressure in the vault;
   exhausting the heated air upward through the exhaust vent stack; and
   passively drawing air from the vault to the flameless heater through the first conduit to replace the heated air.

2. The method of claim 1, wherein during operation, the flameless heater is in continuous, one-way communication with the vault.

3. The method of claim 1 further comprising actively drawing air from the vault to the flameless heater through the first conduit using a mechanical ventilation unit positioned in the first conduit, between the flameless heater and the vault.

4. The method of claim 3, wherein the mechanical ventilation unit comprises a fan.

5. The method of claim 3, further comprising cycling operation of the mechanical ventilation unit and the flameless heater based on a time-dependent schedule.

6. The method of claim 3, further comprising actively drawing air from the vault with the mechanical ventilation unit when the flameless heater is inactive.

7. The method of claim 1, wherein the flameless heater is a catalytic heater.

8. The method of claim 7 further comprising heating the air with a plurality of flameless heaters.

9. The method of claim 1, wherein the flameless heater is positioned at a higher elevation than the vault.

10. The method of claim 9, wherein the second conduit extends upward from the flameless heater such that heated air exhausts above the flameless heater.

11. The method of claim 1, further comprising a substantially enclosed space in fluid communication with the vault, such that passively drawing air from the vault to the flameless heater through the first conduit further comprises passively drawing air from the substantially enclosed space to the flameless heater via the vault and first conduit.

12. The method of claim 11, wherein during operation, the flameless heater is in continuous, one-way communication with the substantially enclosed space.

13. The method of claim 11, further comprising a housing defining the substantially enclosed space, wherein the flameless heater is mounted on the roof of the housing.

14. The method of claim 11, wherein the substantially enclosed space defines a vent such that fresh air is drawn into the substantially enclosed space by the flameless heater.

15. The method of claim 11 further comprising heating the substantially enclosed space with the heated and exhausted air.

16. The method of claim 1 further comprising initializing oxidation of the flameless heater with an electrical resistance heater.

17. The method of claim 1 further comprising pre-heating the air from the vault with the heated air exiting the flameless heater.

* * * * *